(12) United States Patent
Schneider et al.

(10) Patent No.: US 8,778,127 B2
(45) Date of Patent: Jul. 15, 2014

(54) APPARATUSES AND METHODS FOR BONDING SUBSTRATES

(75) Inventors: Uwe Schneider, Cincinnati, OH (US);
David Carlton Ordway, Oxford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 162 days.

(21) Appl. No.: 13/402,056

(22) Filed: Feb. 22, 2012

(65) Prior Publication Data
US 2013/0213547 A1 Aug. 22, 2013

(51) Int. Cl.
| B29C 65/10 | (2006.01) |
| B32B 37/04 | (2006.01) |
| B29C 65/02 | (2006.01) |
| B29C 65/78 | (2006.01) |
| B29L 31/48 | (2006.01) |

(52) U.S. Cl.
CPC ....... B29C 65/026 (2013.01); B29L 2031/4878 (2013.01); B29C 65/7897 (2013.01); B32B 37/04 (2013.01)
USPC .......... 156/309.6; 156/497; 156/499

(58) Field of Classification Search
CPC .. B29C 65/026; B29C 65/7897; B32B 37/04; B29L 2031/4878
USPC ............. 156/308.2, 309.6, 497, 499
See application file for complete search history.

(56) References Cited

U.S. PATENT DOCUMENTS

| 3,860,003 A | 1/1975 | Buell |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |

(Continued)

FOREIGN PATENT DOCUMENTS

WO  WO 2011/156299 A1  12/2011

OTHER PUBLICATIONS

U.S. Appl. No. 13/401,907; P&G, Feb. 22, 2012, Schneider.

(Continued)

*Primary Examiner* — Katarzyna Wyrozebski Lee
*Assistant Examiner* — Scott W Dodds
(74) *Attorney, Agent, or Firm* — Charles R. Matson; Abbey A. Lopez; Sarah M. DeCristofaro

(57) ABSTRACT

A method of joining web portions includes advancing web portions onto a rotating drum such that the web portions overlap at an overlap area as the web portions wrap around the drum. The web portions each have a melting temperature. A fluid is heated to a temperature sufficient to at least partially melt the web portions. A fluid nozzle retracts from an aperture in the drum and a jet of the heated fluid is directed from a fluid nozzle onto the web portions at the overlap area. The heated fluid penetrates and at least partially melts the web portions. The web portions are at least partially melted using the heated fluid. A press member shifts through the aperture in the drum to compress the web portions between the pressure member and an anvil roll to join the web portions together at the overlap area.

10 Claims, 22 Drawing Sheets

(56) References Cited

U.S. PATENT DOCUMENTS

| | | | |
|---|---|---|---|
| 5,562,646 | A | 10/1996 | Goldman et al. |
| 5,599,335 | A | 2/1997 | Goldman et al. |
| 5,628,097 | A | 5/1997 | Benson et al. |
| 5,669,894 | A | 9/1997 | Goldman et al. |
| 5,779,831 | A | 7/1998 | Schmitz |
| 5,916,661 | A | 6/1999 | Benson et al. |
| 6,107,539 | A | 8/2000 | Palumbo et al. |
| 6,248,195 | B1 | 6/2001 | Schmitz |
| 6,545,197 | B1 | 4/2003 | Muller et al. |
| 6,790,798 | B1 | 9/2004 | Suzuki et al. |
| 7,569,039 | B2 | 8/2009 | Matsuda et al. |
| 7,587,966 | B2 | 9/2009 | Nakakado et al. |
| 2004/0097895 | A1 | 5/2004 | Busam et al. |
| 2004/0158212 | A1 | 8/2004 | Ponomarenko et al. |
| 2005/0107764 | A1 | 5/2005 | Matsuda et al. |
| 2011/0151171 | A1* | 6/2011 | Biegler et al. .......... 428/57 |
| 2012/0021186 | A1 | 1/2012 | Schneider |
| 2012/0061015 | A1 | 3/2012 | LaVon et al. |
| 2012/0061016 | A1 | 3/2012 | LaVon et al. |
| 2013/0213547 | A1 | 8/2013 | Schneider et al. |
| 2013/0218116 | A1 | 8/2013 | Schneider et al. |

OTHER PUBLICATIONS

International Search Report, PCT/US2013/026980 dated May 29, 2013, 9 pages.
U.S. Appl. No. 13/401,907, filed Feb. 22, 2012, Blessing, et al.
U.S. Appl. No. 14/038,812, filed Sep. 27, 2013, Franke, et al.

* cited by examiner

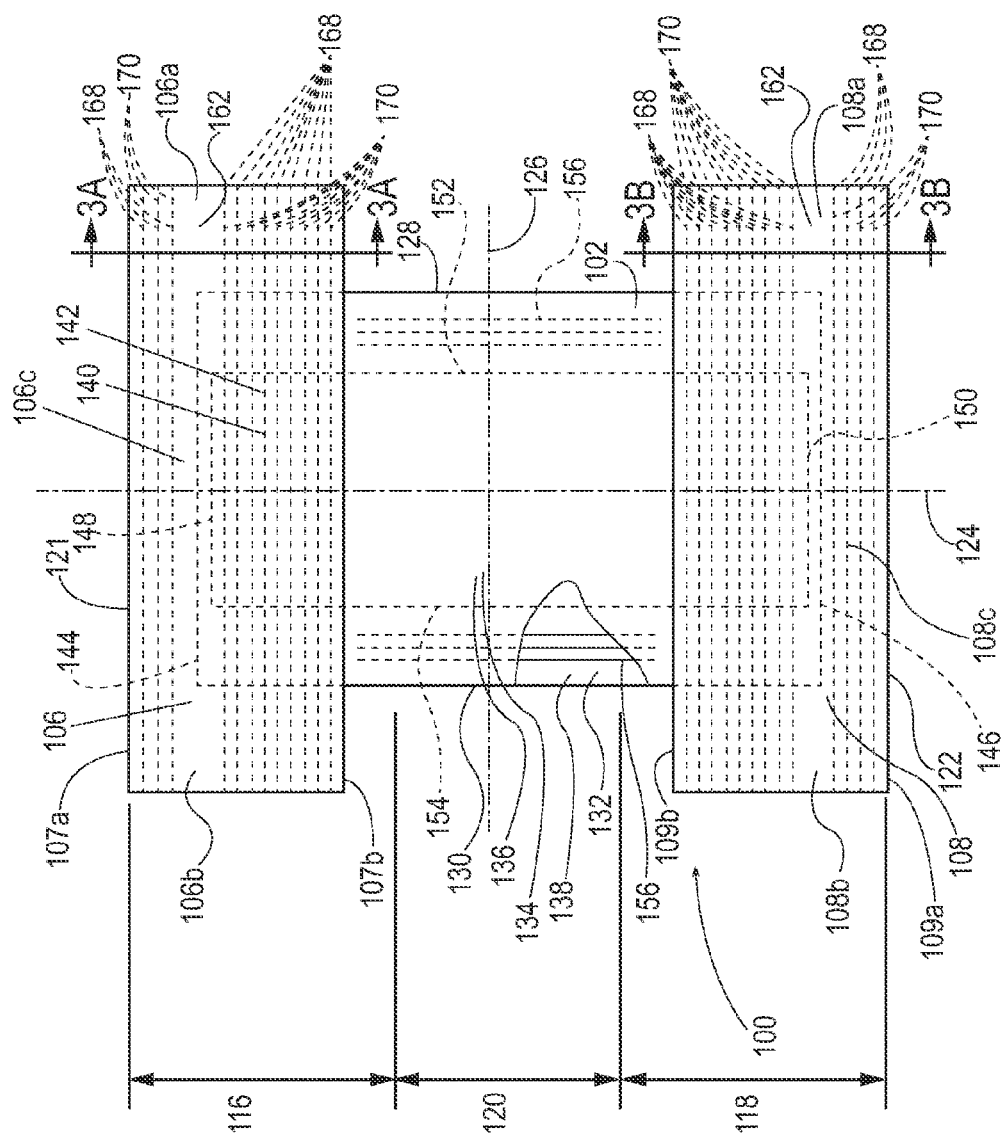

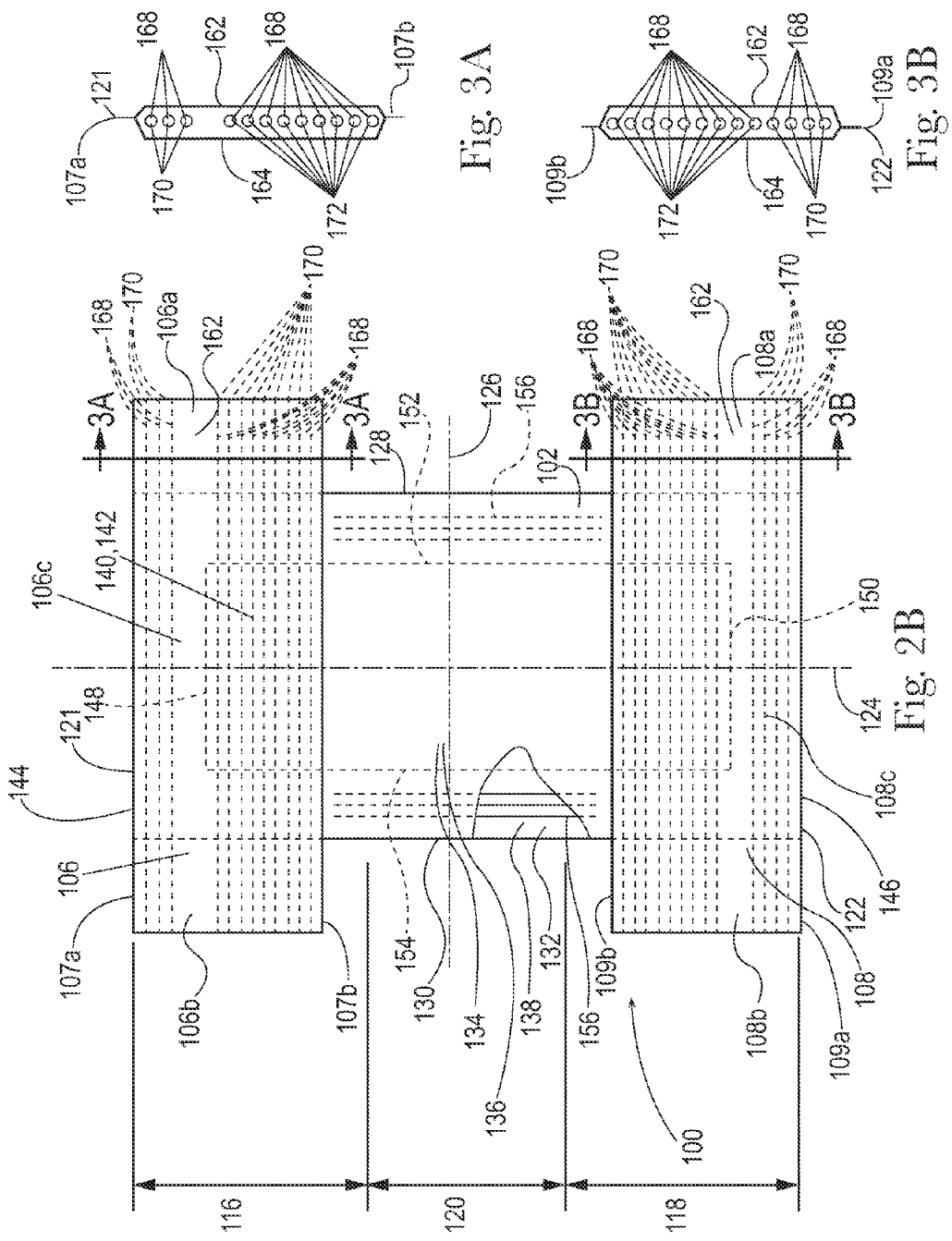

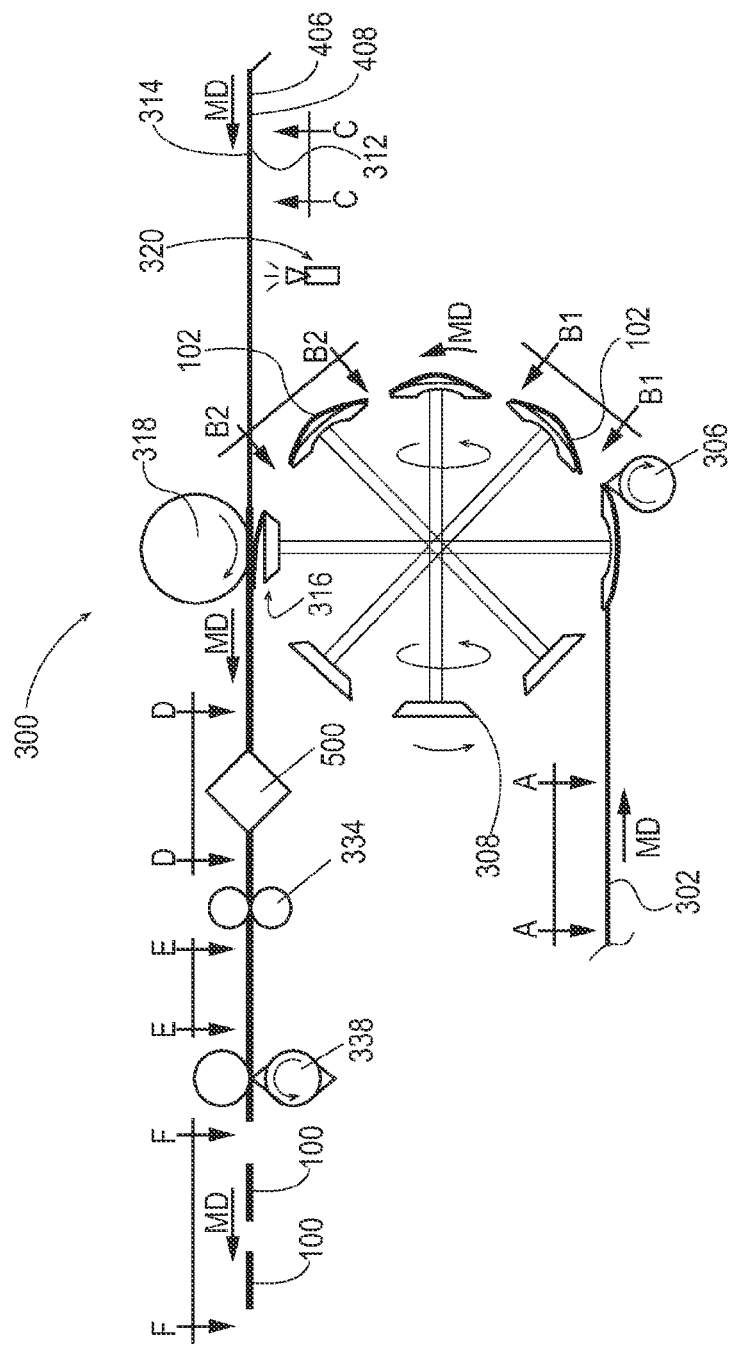

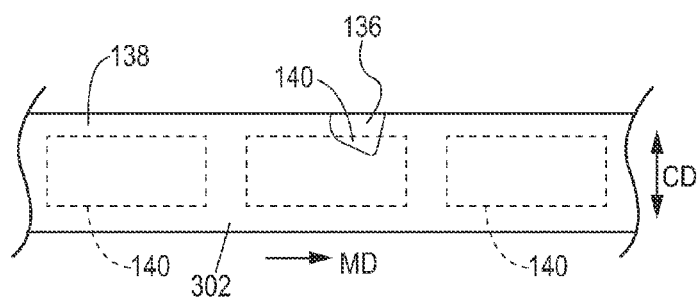
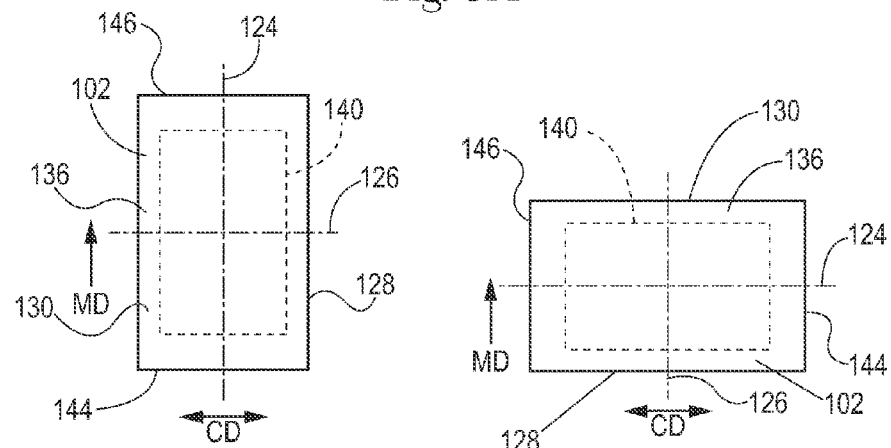
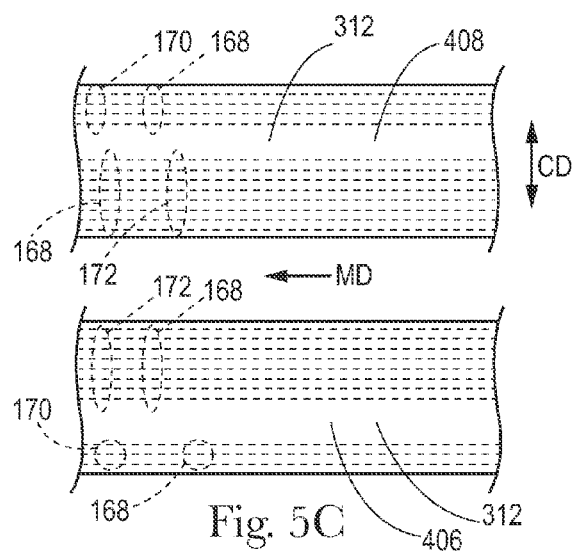

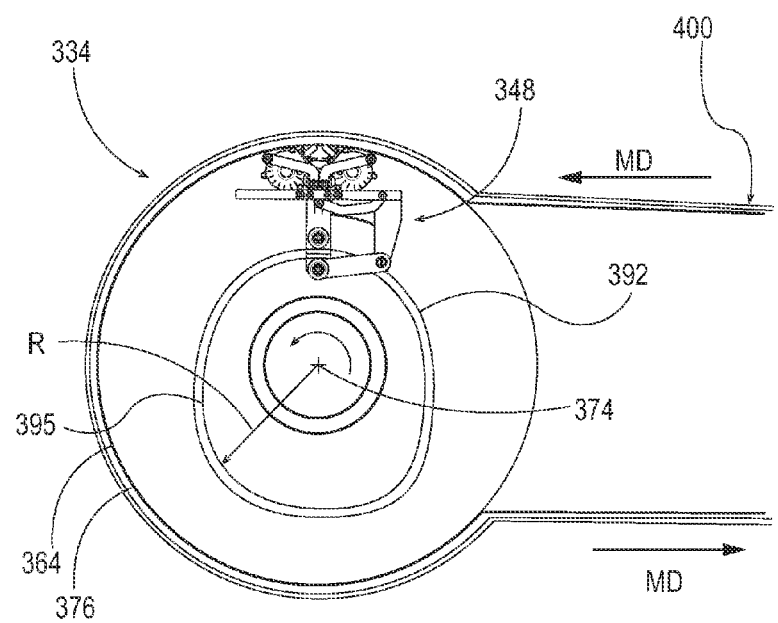
Fig. 6A1

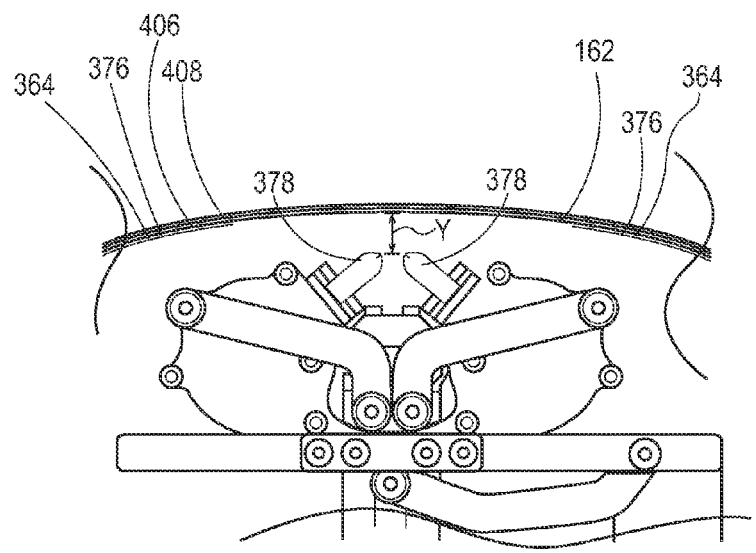
Fig. 6B1

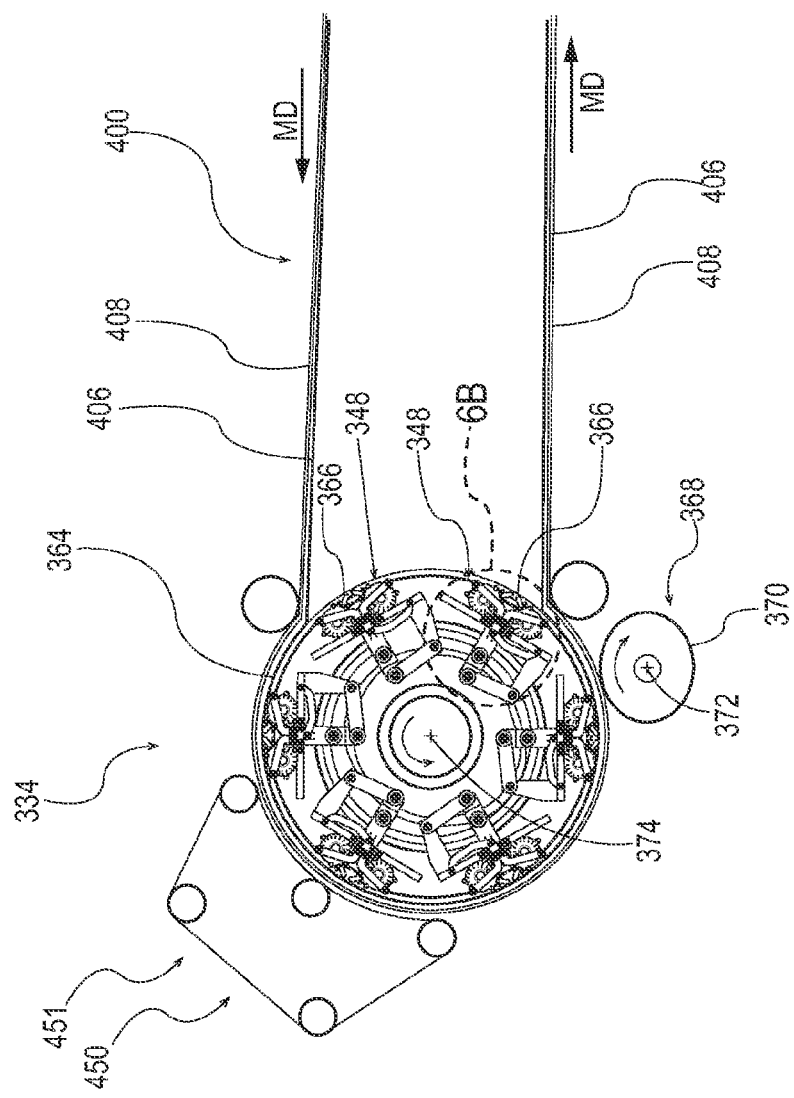

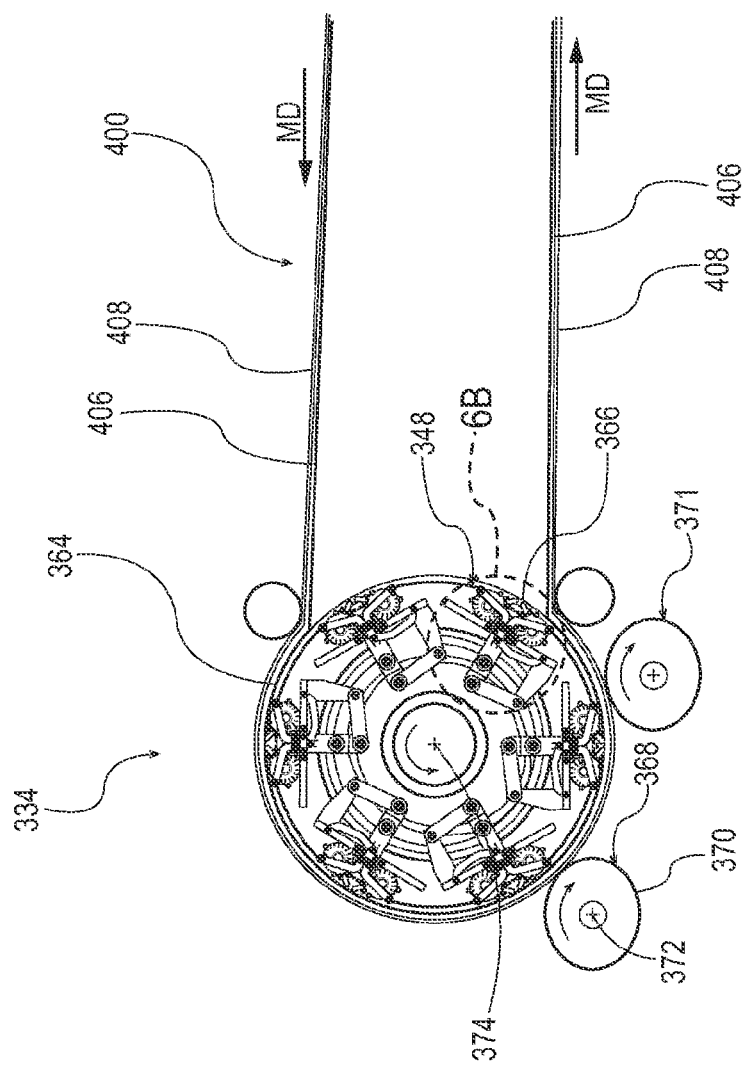

APPARATUSES AND METHODS FOR BONDING SUBSTRATES

FIELD OF THE INVENTION

The present disclosure relates to methods for manufacturing absorbent articles, and more particularly, to apparatuses and methods for bonding components together during the manufacture of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some converting configurations, discrete chassis spaced apart from each other are advanced in a machine direction and are arranged with a longitudinal axis parallel with the cross direction. Opposing waist regions of discrete chassis are then connected with continuous lengths of elastically extendable front and back belt webs advancing in the machine direction. While connected with the chassis, the front and back belt webs are maintained in a fully stretched condition along the machine direction, forming a continuous length of absorbent articles. The continuous length of absorbent articles may then be folded in a cross direction. During the folding process in some converting configurations, one of the front and back belt webs is folded into a facing relationship with the opposing belt. The front and back belts may then be bonded together to create the side seams on diapers.

Consequently, it would be beneficial to provide methods and apparatuses for more precisely controlling the location and strength of bonds used to form the side seams.

SUMMARY OF THE INVENTION

Aspects of the present disclosure involve apparatuses and methods for manufacturing absorbent articles, and more particularly, methods for seaming webs during the manufacture of disposable absorbent articles. Particular embodiments of methods of manufacture disclosed herein provide for forming side seams in various types of diaper configurations. While the present disclosure relates mainly to forming side seams in diaper pants, it is to be appreciated that the methods and apparatuses disclosed herein can also be applied to other seams used on diapers as well as other types of absorbent articles.

In one embodiment, a method for forming a seam includes the steps of: rotating a drum about an axis of rotation, the drum comprising a fluid nozzle and a press member; rotating an anvil roll adjacent the drum; advancing a first substrate in a machine direction onto the drum, the first substrate having an inner surface and an outer surface, wherein the outer surface of the first substrate is adjacent the drum; advancing a second substrate in the machine direction, wherein the first substrate is between the second substrate and the drum; wrapping the first and second substrates around a portion of the drum; heating a fluid to a temperature sufficient to at least partially melt substrates; moving the fluid nozzle radially outward from the drum; directing a jet of the heated fluid onto the first and second substrates; partially melting the first and second substrates; retracting the fluid nozzle radially inward into the drum; shifting the press member radially outward from the drum; and compressing the first and second substrates between the press member and the anvil roll.

In another embodiment, an apparatus for bonding substrates together includes a drum for continuously advancing a first and a second substrate. The drum comprises a drum outer circumferential surface and a drum aperture in the drum outer circumferential surface. The drum is adapted to rotate about an axis of rotation. The apparatus comprises a fluid nozzle moveably connected to the drum, located radially inward from the drum aperture, and adapted to direct fluid radially outward through the drum aperture toward the first and second substrates. The apparatus also comprises an anvil roll located adjacent the drum, the anvil roll adapted to rotate about an axis of rotation. The apparatus further comprises a press member moveably connected to the drum, located radially inward from the drum aperture, and adapted to extend through the drum aperture to compress the first and second substrates between the anvil roll to form a bond.

BRIEF DESCRIPTION OF THE DRAWINGS

FIG. 2A is a partially cut away plan view of the diaper pant shown in FIG. 1.

FIG. 2B is a partially cut away plan view of a second embodiment of a diaper pant.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 4 is a schematic side view of a converting apparatus adapted to manufacture pre-fastened, pant diapers.

FIG. 5A is a view of a continuous length of chassis assemblies from FIG. 4 taken along line A-A.

FIG. 5B1 is a view of a discrete chassis from FIG. 4 taken along line B1-B1.

FIG. 5B2 is a view of a discrete chassis from FIG. 4 taken along line B2-B2.

FIG. 5C is a view of continuous lengths of advancing front and back side panel material from FIG. 4 taken along line C-C.

FIG. 6A1 is a detailed, schematic side view of the bonder apparatus of FIG. 6A.

FIG. 6B1 is a detailed elevation view of the seamer station of FIG. 6B.

FIG. 6C is an schematic side view of another embodiment of a bonder apparatus adapted to seam pre-fastened diapers.

FIG. 6D is a schematic side view of another embodiment of a bonder apparatus adapted to seam pre-fastened diapers.

DETAILED DESCRIPTION OF THE INVENTION

Figure 1:
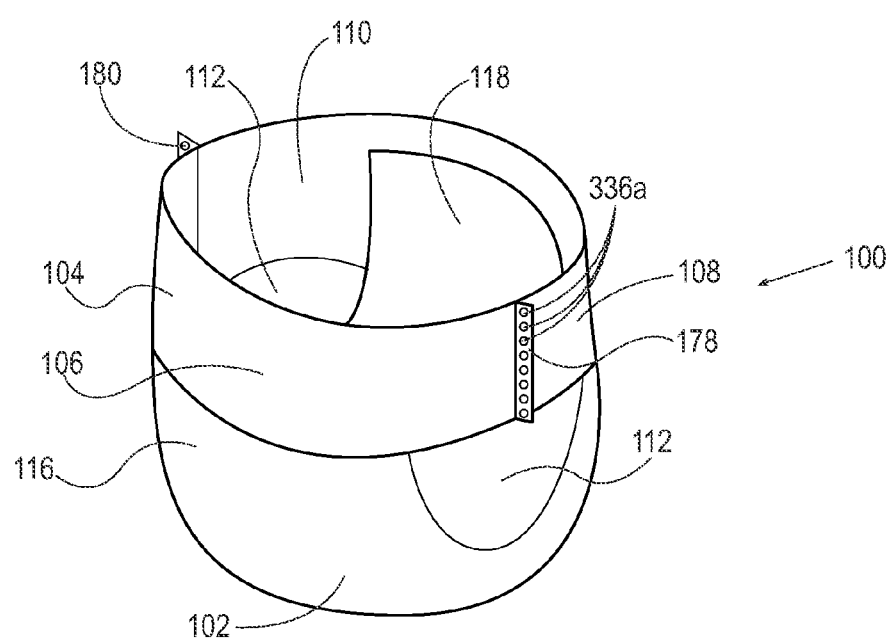
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Radial" means a direction running from the center of a drum toward a drum outer circumferential surface.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The present disclosure relates to methods and apparatuses for bonding substrates together. As discussed in more detail below, the bonding apparatuses may include a drum and an anvil roll adjacent the drum. The anvil roll and the drum may each include an outer circumferential surface. The drum may also include an aperture in the outer circumferential surface and one or more seaming stations located radially inward from the outer circumferential surface of the drum. As discussed in more detail below, the seaming station may include a fluid nozzle operatively connected with a press member. During the bonding operation, the drum is rotated about an axis of rotation and a first substrate advances in a machine direction MD onto the outer circumferential surface of the drum. A second substrate is also advanced in the machine direction MD, wherein the first substrate is between the second substrate and the drum. A fluid is heated to a temperature sufficient to at least partially melt the substrates. As the drum rotates, the fluid nozzle moves radially outward toward the aperture in the outer circumferential surface of the drum. The fluid nozzle directs a jet of the heated fluid through the aperture and onto an overlap area of the first and second substrates, which partially melts the overlap area. As the drum continues to rotate, the fluid nozzle retracts radially inward from the aperture, and the press member moves radially outward through the aperture. The partially melted overlap area is then compressed between the press member and the anvil roll, creating a discrete bond region or seam between the first and second substrates. The drum continues to rotate and the press member retracts radially inward from the aperture.

As discussed below, the bonding apparatuses may be configured to partially melt and compress the substrates while traveling on the drum to minimize deformation to weak, partially melted substrates as the substrates advance in the machine direction MD. The operative connection between the fluid nozzle and the press member may be configured to partially melt and compress the substrates at the same relative location in order to create discrete bond sites. In some configurations, the press member may also include a spring member to apply a predetermined force to the overlap area between the press member and the anvil roll.

It is to be appreciated that although the bonding methods and apparatuses herein may be configured to bond various types of substrates, the methods and apparatuses herein are discussed below in the context of manufacturing absorbent articles. In particular, the methods and apparatuses are discussed in the context of bonding belt substrates together to form side seams of advancing, continuous lengths of absorbent articles during production. As discussed below, an advancing continuous length of absorbent articles may include a plurality of chassis connected with a continuous first belt substrate and a continuous second belt substrate. The continuous first and second belt substrates may be separated from each other along a cross direction while advancing along a machine direction MD. Each chassis may extend in the cross direction CD and may include opposing first and second end regions separated by a central region, wherein the first end regions are connected with first belt substrate and the second end regions are connected with the second belt substrate. The chassis may also be spaced from each other along the machine direction MD. A folding apparatus operates to fold the chassis around the folding axis along the central regions and to bring the second belt substrate and second end region of the chassis into a facing relationship with the first belt substrate and first end region of the chassis. In some embodiments, the first belt substrate, second belt substrate, folded chassis advance in the machine direction to onto the outer circumferential surface of a rotating drum such as described above. As the drum rotates, a fluid nozzle moves radially outward toward an aperture in the outer circumferential surface of the drum. The fluid nozzle directs a jet of the heated fluid through the aperture and onto an overlap area of the first and second belt substrates, which partially melts the overlap area. As the drum continues to rotate, the fluid nozzle retracts radially inward from the aperture, and the press member moves radially outward through the aperture. The partially melted overlap area is then compressed between the press member and an anvil roll, creating discrete bond sites or seams between the first and second belt substrates. The drum continues to rotate and the press member retracts radially inward from the aperture, and the continuous length of first and second belt substrates are advanced from the drum to a knife roll. The bonded regions are cut by the knife roll along the cross direction to create a first side seam on an absorbent article and a second side seam on a subsequently advancing absorbent article.

As previously mentioned, the processes and apparatuses discussed herein may be used to bond various types of substrate configurations, some of which may be used in the manufacture of different types of absorbent articles. To help provide additional context to the subsequent discussion of the process embodiments, the following provides a general description of absorbent articles in the form of diapers that include components that may be bonded in accordance with the methods and apparatuses disclosed herein.

FIGS. 1 and 2A show an example of a diaper pant 100 that may be assembled and folded in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented toward the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2A are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 140 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. patent application Ser. No. 12/434,984.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 116 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 107b may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

As previously mentioned, the apparatuses and methods according to the present disclosure may be utilized to assemble various components of pre-fastened, refastenable pant diapers 100. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1 and 2A. Although the following methods are provided in the context of the diaper 100 shown in FIGS. 1 and 2A, it is to be appreciated that various embodiments of diaper pants can be manufactured according to the methods disclosed herein, such as for example, the absorbent articles disclosed in U.S. Pat. No. 7,569,039, filed on Nov. 10, 2004; U.S. Patent Publication No. 2005/0107764A1, filed on Nov. 10, 2004; U.S. patent application Ser. No. 13/221,127, filed on Aug. 30, 2011; and U.S. patent application Ser. No. 13/221,104, filed on Aug. 30, 2011, which are all hereby incorporated by reference herein.

As described in more detail below, the converting apparatus 300 shown in FIG. 4 operates to advance discrete chassis 102 along a machine direction MD such that the lateral axis of each chassis 102 is parallel with the machine direction, and wherein the chassis 102 are spaced apart from each other along the machine direction. Opposing waist regions 116, 118 of the spaced apart chassis 102 are then connected with continuous lengths of advancing first and second elastic belt substrates 406, 408. The chassis 102 are then folded along the lateral axis to bring the first and second elastic belt substrates 406, 408 into a facing relationship, and the first and second elastic belt substrates are connected together along regions 336 intermittently spaced along the machine direction, wherein each region 336 may include one or more discrete bond sites 336a. And the elastic belt substrates 406, 408 are cut along the regions 336 to create discrete diapers 100, such as shown in FIG. 1.

As shown in FIGS. 4 and 5A, a continuous length of chassis assemblies 302 are advanced in a machine direction MD to a carrier apparatus 308 and cut into discrete chassis 102 with knife roll 306. The continuous length of chassis assemblies may include absorbent assemblies 140 sandwiched between topsheet material 138 and backsheet material 136, leg elastics, barrier leg cuffs and the like. A portion of the chassis assembly is cut-away to show a portion of the topsheet material 138 and an absorbent assembly 140.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the second longitudinal side edge 130 is the leading edge and the first longitudinal side edge 128 is the trailing edge.

As discussed below with reference to FIGS. 3, 5C, 5D, 5E, and 5F, the chassis 102 are transferred from the carrier apparatus 308 and combined with advancing, continuous lengths of belt substrates 406, 408, which are subsequently cut to form first and second elastic belts 106, 108 on diapers 100.

With reference to FIGS. 3 and 5C, the chassis 102 are transferred from the carrier apparatus 308 to a nip 316 between the carrier apparatus 308 and a carrier apparatus 318 where the chassis 102 is combined with continuous lengths of advancing front belt 406 and back belt 408 substrate material. The front belt substrate material 406 and the back belt substrate material 408 each define a wearer facing surface 312 and an opposing garment facing surface 314. The wearer facing surface 312 of the first belt substrate 406 may be combined with the garment facing surface 134 of the chassis 102 along the first waist region 116, and the wearer facing surface 312 of the second belt substrate 408 may be combined with the garment facing surface 134 of the chassis 102 along the second waist region 118. As shown in FIG. 4, adhesive 320 may be intermittently applied to the wearer facing surface 312 of the first and second belt substrates 406, 408 before combining with the discrete chassis 102 at the nip 316 between roll 318 and the carrier apparatus 308.

Figure 5D:
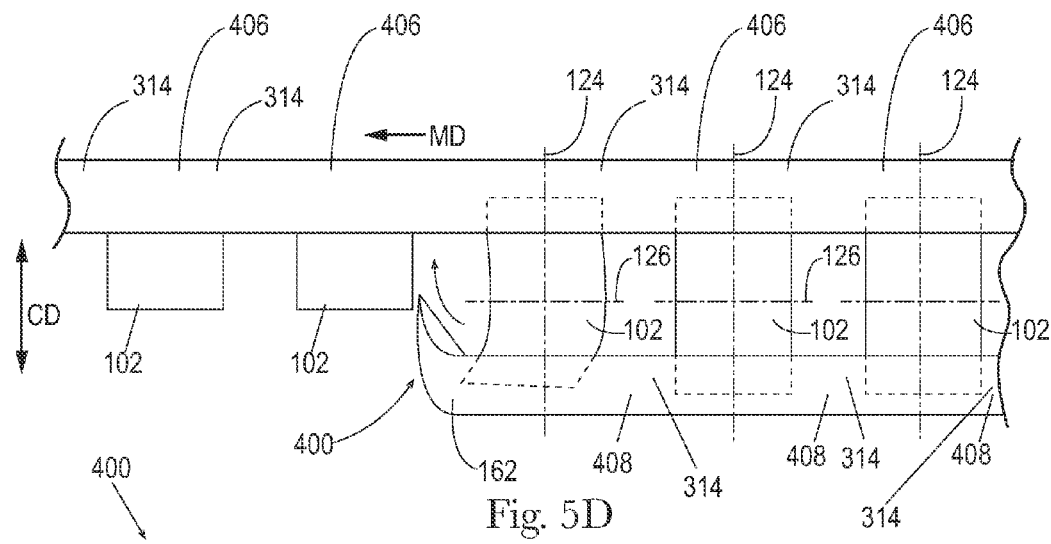
FIG. 5D is a view of multiple discrete chassis spaced from each other along the machine direction MD and connected with each other by the front and back side panel material from FIG. 4 taken along line D-D.
Figure 5E:
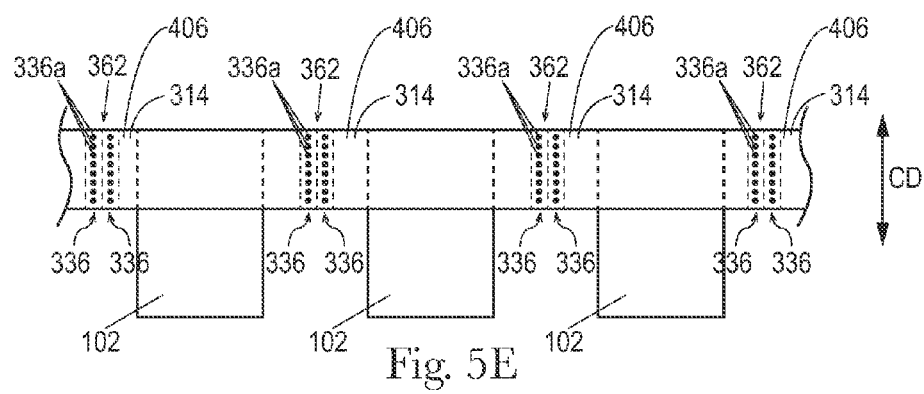
FIG. 5E is a view of folded multiple discrete chassis with the front and back side panel material in a facing relationship from FIG. 4 taken along line E-E.
Figure 5F:
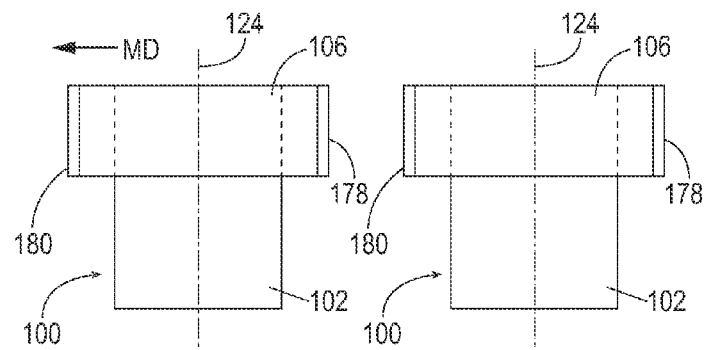
FIG. 5F is a view of two discrete absorbent articles advancing the machine direction MD from FIG. 4 taken along line F-F.

With reference to FIGS. 4 and 5D, a continuous length of absorbent articles 400 are defined by multiple discrete chassis 102 spaced from each other along the machine direction MD and connected with each other by the second belt substrate 408 and the first belt substrate 406. As shown in FIG. 4, the continuous length of absorbent articles 400 advances from the nip 316 to a folding apparatus 500. At the folding apparatus 500, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt substrate 408 extending between each chassis 102 in a facing relationship with the wearer facing surface 312 of the first belt substrate 406 extending between each chassis 102. As shown in FIGS. 4, 5D, and 5E, the folded discrete chassis 102 connected with the first and second belt substrates 406, 408 are advanced from the folding apparatus 500 to a bonder apparatus 334. The bonder apparatus 334 operates to bond an overlap area 362, thus creating discrete bond sites 336a. The overlap area 362 includes a portion of the second belt substrate 408 extending between each chassis 102 and a portion of the first belt substrate 406 extending between each chassis 102. As shown in FIGS. 4 and 5F, a continuous length of absorbent articles are advanced from the bonder 334 to a knife roll 338 where the regions 336 are cut into along the cross direction to create a first side seam 178 on an absorbent article 100 and a second side seam 180 on a subsequently advancing absorbent article.

Although the absorbent article is described as having a first and second belt substrate, it is to be appreciated that the absorbent article may have only one belt substrate. Further, it is to be appreciated that the chassis and belt substrate of the absorbent article may be one continuous substrate such that the overlap area is formed from the same substrate. As such, the bonder apparatus may operate to bond a continuous substrate at an overlap area to form one or more discrete bond sites.

Figure 6A:
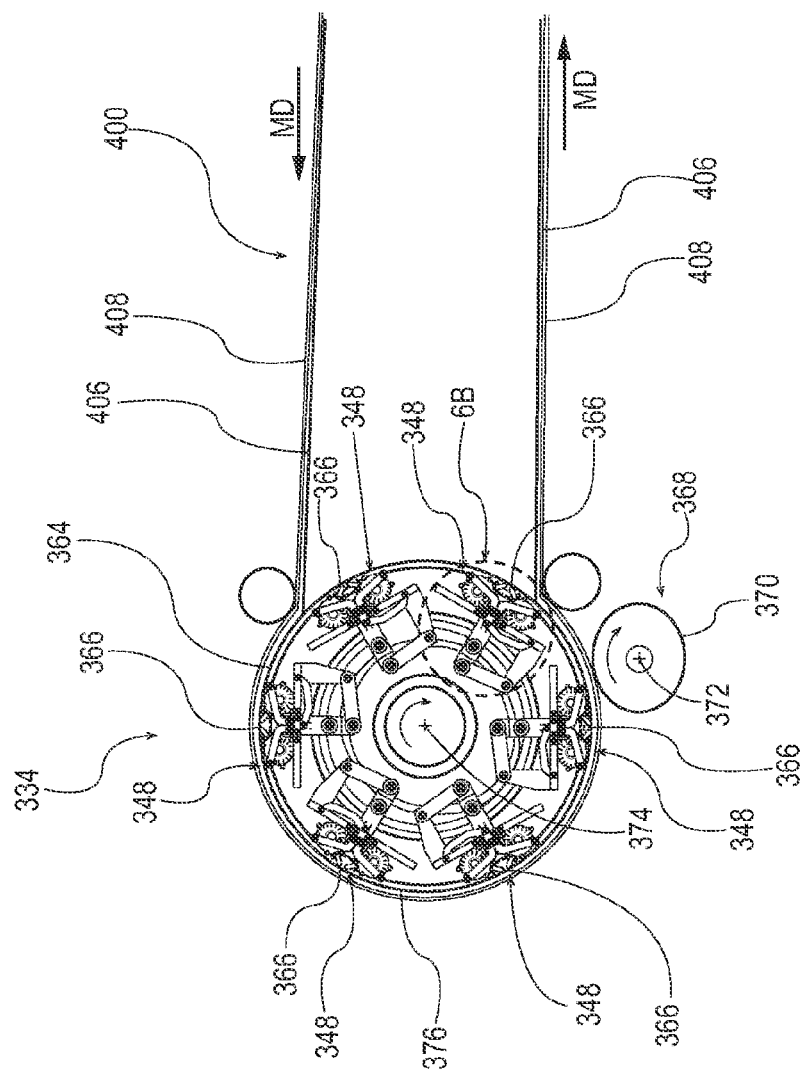
FIG. 6A is a schematic side view of a bonder apparatus adapted to seam pre-fastened pant diapers.

As previously mentioned, with reference to FIG. 4, the converting apparatus may include a bonder apparatus 334. For example, FIG. 6A shows a detailed schematic side view of an embodiment of a bonder apparatus 334 that may be used with the methods and apparatuses herein. As shown in FIG. 6A, the bonder apparatus 334 may include a drum 364 and an anvil roll 368 located adjacent the drum 364. The anvil roll 368 includes an anvil roll outer circumferential surface 370 and is adapted to rotate about an anvil roll axis of rotation 372. The drum 364 may also include a drum outer circumferential surface 376 and is adapted to rotate about a drum axis of rotation 374. The drum 364 may also include one or more drum apertures 366 in the drum outer circumferential surface 376. In addition, a plurality of seaming stations 348 are positioned radially inward from the drum outer circumferential surface 376 and the drum apertures 366. As discussed in more detail below, with reference to FIG. 6B, each seaming station 348 may include a fluid nozzle 378 and a press member 380. Although the drum 364 shown in FIG. 6A includes six seaming stations 348, it is to be appreciated that the drum 364 may be configured to include more or less than six seaming stations 348.

Figure 6B:
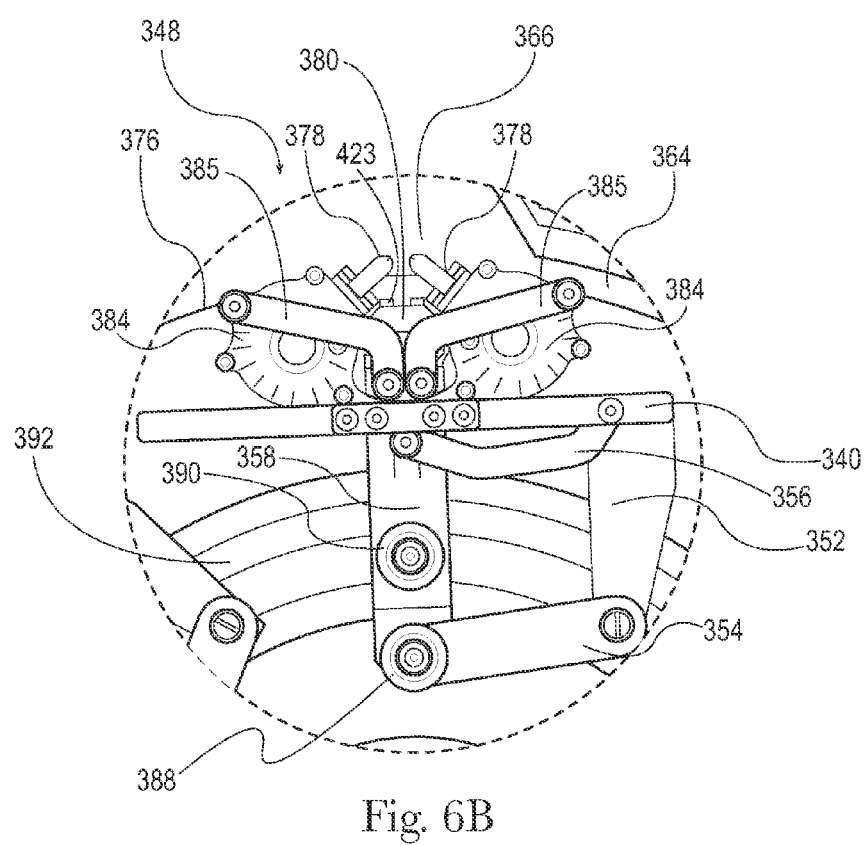
FIG. 6B is an elevation view of the seamer station of FIG. 6A.

During operation, the drum 364 may rotate about the drum axis of rotation 374 and the anvil roll 368 may rotate about the anvil roll axis of rotation 372 in the directions shown in FIG. 6A. Absorbent articles 400 may advance in machine direction MD onto the drum outer circumferential surface 376, wherein the first belt substrate 406 is between the second belt substrate 408 and the drum outer circumferential surface 376. As the drum 364 rotates, fluid nozzles 378 of a seaming station 348 move radially outward toward the drum aperture 366 in the drum outer circumferential surface 376 as shown in FIG. 6B. In addition, a fluid is heated to a temperature sufficient to at least partially melt the overlap area. The fluid nozzles direct a jet of the heated fluid through the drum aperture 366 and onto an overlap area of the first and second substrates 406, 408, which partially melts the overlap area 362. As the drum 364 continues to rotate, the fluid nozzles retract radially inward from the drum aperture 366, the drum 112 continues t rotates about the drum axis of rotation 374, and a press member shifts radially outward through the drum aperture 366. The press member then compresses the partially melted overlap area against the anvil roll outer circumferential surface 370, creating one or more discrete bond sites 336a between the first and second belt substrates 406, 408. As the drum 364 continues to rotate, the press member retracts radially inward from the drum aperture 366.

Figure 7:
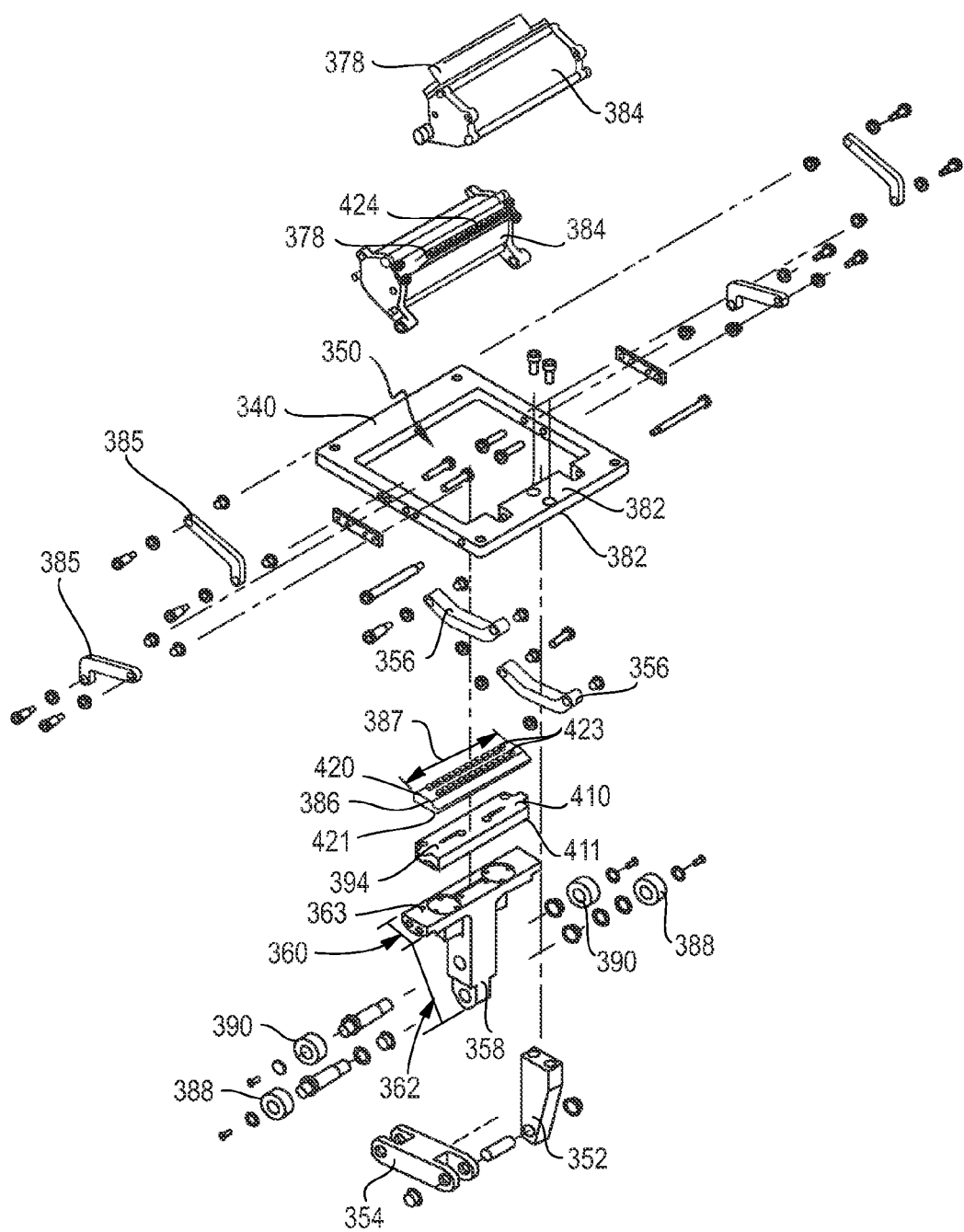
FIG. 7 is a detailed, exploded view of an embodiment of a seaming apparatus.

As previously mentioned, each seaming station of the drum may include a fluid nozzle and a press member. FIG. 7 shows a detailed exploded view of an embodiment of a seaming station 348. As shown in FIG. 7, the seaming station 348 includes a base member 340 that is immovably connected with and rotates with the drum. The base member 340 is substantially square shaped and is defined by a base member top surface 382 and a base member bottom surface 383. The base member 340 includes a base aperture 350 extending through the base member top and bottom surfaces 382, 383 such that a fluid nozzle 384 and press member 386 may extend through the base aperture 350. Moreover, the base member bottom surface 383 is immovably connected with a base link 352. As discussed below, one end of the base link 352 is connected to the base member bottom surface 383, and another end of the base link 352 is operatively connected to a first shifting link 354.

With continuing reference to FIG. 7, the seaming station 348 also includes a cam follower member 358 and first and second sets of cam rollers 388, 390 rollingly connected with the cam follower member 358. The cam follower member 358 is substantially T-shaped, and is defined by a cam follower member first portion 360, a cam follower member second portion 362, and a cam follower member top face 363. The cam follower member first portion 360 is operatively connected with the first shifting link 354 and the first set of cam rollers 388 at the same position on the cam follower member 358. Furthermore, the second set of cam rollers 390 is operatively connected to the cam follower member second portion 362 at a position radially outboard from the first set of cam rollers 388. Also operatively connected to the cam follower member 358 is a set of second shilling links 356. The set of second shifting links 356 operatively connects the base member 340 to the cam follower member first portion 360 at a position relatively outboard of the second set of cam rollers 390.

As discussed in more detail below, with reference to FIGS. 6A1 and 6B, the first and second set of cam rollers 388, 390 are configured to roll along a stationary cam track as the drum 364 rotates. The stationary cam track 293 surrounds the axis of rotation 374 and is defined by an inner circumferential surface 395 and a radius R that extends from the inner circumferential surface 395 of the stationary cam track 392 to the axis of rotation 374 as shown in FIG. 6A1. In some embodiments, the stationary cam track 392 may include various curved and/or straight regions such that the stationary cam track 392 is defined by relatively longer and shorter radii R at different points along the inner circumferential surface 395 of the stationary cam track 392. First and second sets of cam rollers 388, 390 roll on the stationary cam track 392 as the drum 364 rotates. The first, second, and third shifting links 354, 356, 385 pivot where the radius R of the stationary cam track 392 increases or decreases as the first and second set of cam rollers 388, 390 roll along the stationary cam track 392. At the same time, in regions where the stationary cam track 392 is defined by relatively longer radii, R, the cam follower member 385 shifts radially outward through the base aperture. Whereas, in regions where the stationary cam track 392 is defined by relatively shorter radii, R, the cam follower member shifts radially inward through the base aperture. It is to be appreciated that the cam track 392 may be configured to have various other shapes and sizes. For example, in some embodiments, the cam track 392 may be configured to have a circular shape that is offset or eccentric with respect to the axis of rotation 374. Offsetting the stationary cam track from the axis of rotation causes the cam follower member to shift as the first and second sets of cam rollers roll along the stationary cam track.

Figure 8:
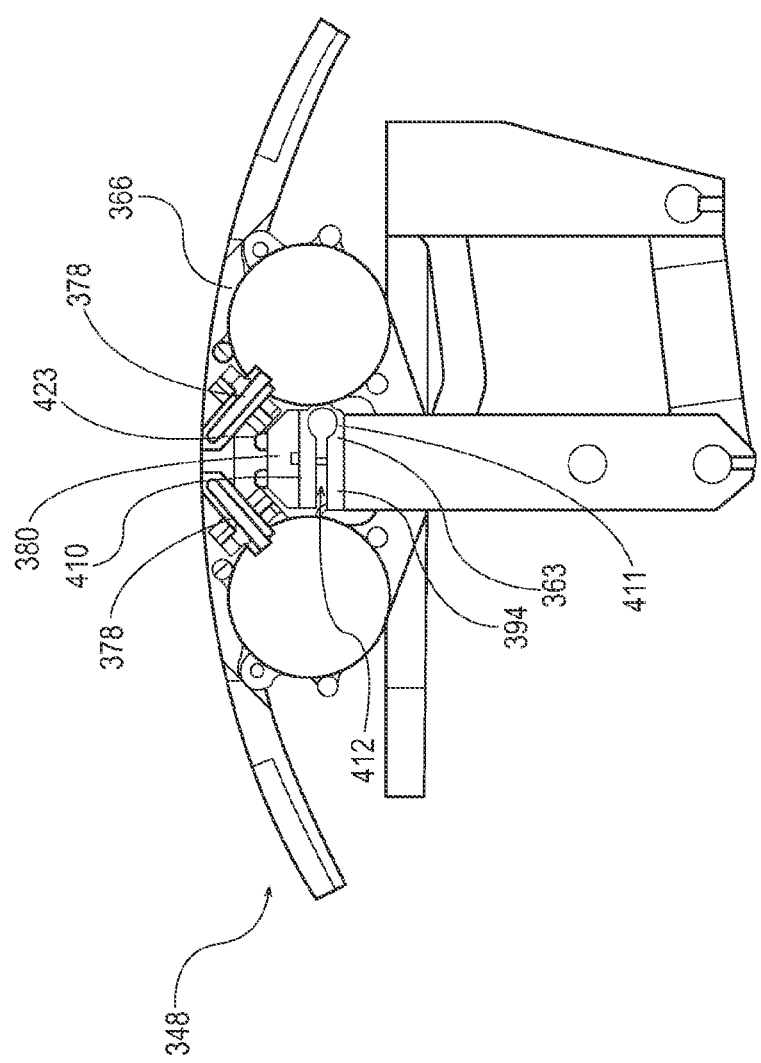
FIG. 8 is an elevation view of an embodiment of a seaming station.

FIG. 8 shows an elevation view of an embodiment of a seaming station 348. With reference to FIGS. 7 and 8, the seaming station 348 may further include a spring member 394. The spring member 394 may be substantially U-shaped and defined by a spring member top face 410, a spring member bottom face 411, and a spring member side opening 412. With reference to FIG. 7, the spring member bottom face 411 is fixedly connected to the cam follower member top face 363. The spring member 394 may extend along the entirety of the cam follower member top face 363. As discussed in further detail below, the spring member side opening 412 allows the spring member 394 to flex as a press member compresses the partially melted overlap area against the anvil roll outer circumferential surface.

As previously discussed, the seaming station may also include a press member 380 as shown in FIG. 7. The press member 380 may be substantially rectangular in shape and defined by a press member top face 420, a press member bottom face 421, and a press member length 387. The press member 380 may include substantially square-shaped projections 423 extending outwardly from the press member top face 420. The press member 421 bottom face is immovably connected to the spring member top face 410. The press member 380 may extend along the entirety of the spring member top face 410. As discussed in more detail below, the projections 423 may be arranged into two rows as shown in FIG. 7.

With continuing reference to FIG. 7, the seaming station 348 may also include two heating apparatuses 384. As discussed in more detail below, each heating apparatus 384 provides a pressurized fluid source for delivery of heated, pressurized fluid, such as air for example, to the fluid nozzle 378. In some embodiments, a valve may control egress of the fluid from the heating apparatus 384 and into a fluid nozzle 378. Each heating apparatus 384 is operatively connected to the base member 380 by a set of third shifting links 385. Each third shifting link 385 is operatively connected to one end of one heating apparatus 384 and also to the can follower member second portion 362.

With reference to FIG. 7 and as discussed above, the seaming station may also include a fluid nozzle 378. The fluid nozzle 378 may include one or more fluid orifices 424 where the heated, pressurized fluid is released from the fluid nozzle 378. Each heating apparatus 384 is immovably connected with a separate fluid nozzle 378. As shown in FIG. 7, the fluid orifices 424 may be circular and may extend in a row along the fluid nozzle 378.

As previously discussed, absorbent articles are advanced in the machine direction MD to a bonder apparatus 334. With reference to FIG. 6A, the absorbent articles 400 advance in the machine direction MD onto a drum outer circumferential surface 376 as the drum 364 is rotating about the drum axis of rotation 374. The first belt substrate 406 is between the second belt substrate 408 and the drum outer circumferential surface 376. More particularly, the outer layer 162 of the first belt substrate 406 may be in direct contact with the drum outer circumferential surface 376. And the inner layer 164 of the first belt substrate 406 may be in direct contact with the inner layer 164 of the second belt substrate 408. The drum outer circumferential surface 376 is traveling at the same speed as the advancing absorbent articles 400 such that the position the absorbent articles 400 are received on the drum outer circumferential surface 376 remains constant until the absorbent articles 400 are removed from the drum 364 downstream. The overlap area of the first and second belt substrates 406, 408 is positioned on the drum outer circumferential surface 376 coincident with a drum aperture 366. As discussed in more detail below, a seaming station 348, located radially inward from the drum aperture 366, is configured to bond a portion of the overlap area as the absorbent articles 400 travel along the drum 364. The seaming station 348 is arranged in a first configuration as the absorbent articles are received on the drum 364.

Figure 9:
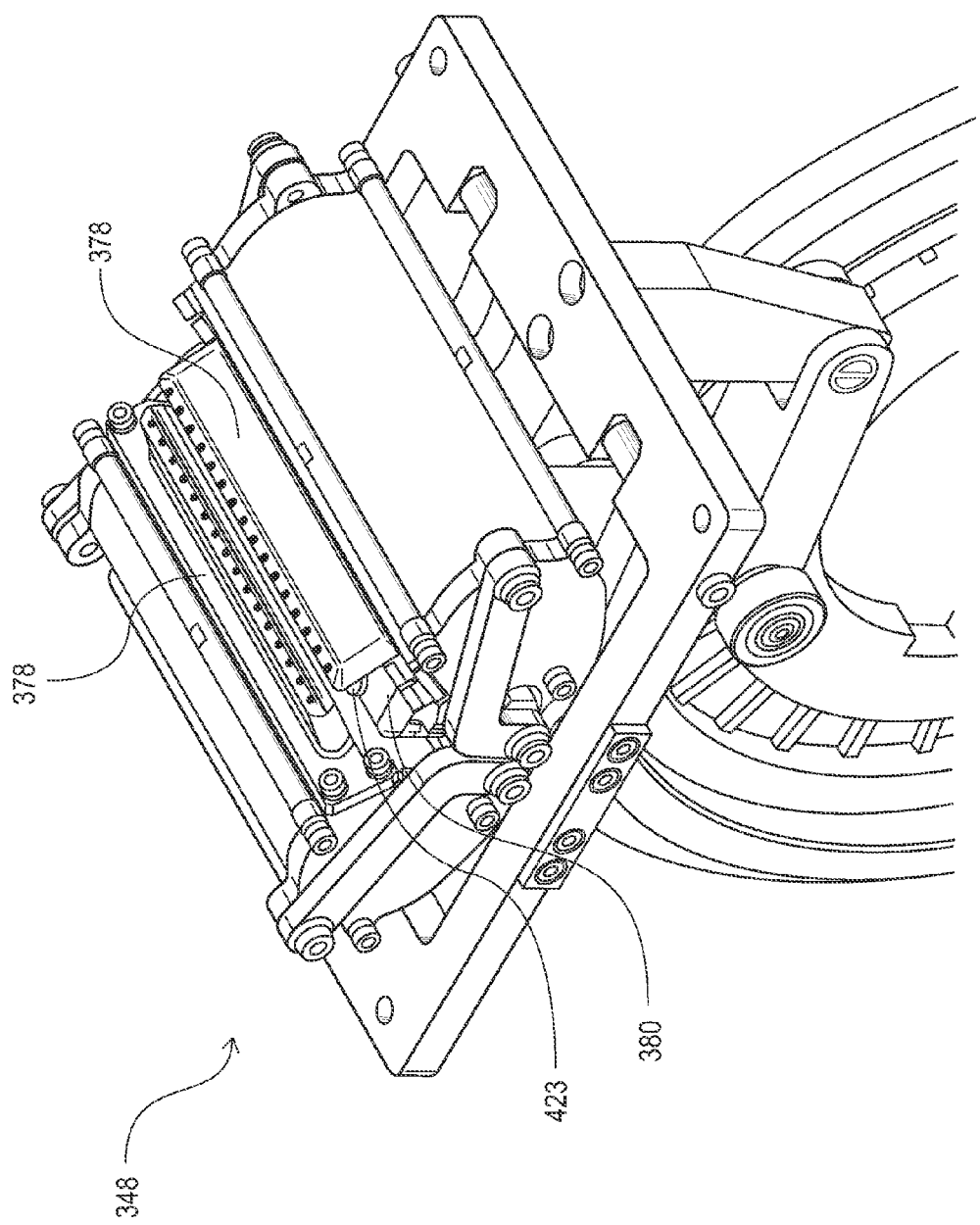
FIG. 9 is a perspective view of an embodiment of a seaming station in a first configuration.

FIG. 9 shows a perspective view of an embodiment of a seaming station 348 in a first configuration. With reference to FIGS. 8 and 9, in the first configuration, the fluid nozzles 378 are positioned radially outward near the drum aperture 366 and drum outer circumferential surface 376, while the press member 380 is positioned radially inward, away from the drum aperture 366 and the drum outer circumferential surface 376. In addition, the fluid nozzles 378 are positioned at the same circumferential location as the projections 423 of the press member 386, such that the heated fluid is directed to the same locations on the overlap area that will subsequently be compressed by the press member 380.

With reference to FIGS. 6A and 6B, as the drum 364 continues to rotate, the absorbent articles 400 wrap around the drum outer circumferential surface 376. At the same time, a jet of heated, pressurized fluid is directed from the heating apparatuses 384 out of the fluid nozzles 378 and onto the overlap area of the first and second belt substrates 406, 408. The fluid nozzles 378 are maintained a preselected distance Y from the outer layer 162 of the first belt substrate 406 to control the pressure applied to the overlap area by the heated fluid as shown in FIG. 6B1. In some embodiments, the distance Y between the outer layer 162 of the first belt substrate 406 and the fluid nozzles 378 may be maintained within 3 mm of the preselected distance Y.

A position control apparatus may be used to maintain the absorbent articles within a constant distance from the outer circumferential surface of the drum as the fluid is heating the overlap area. In some embodiments, the position control apparatus 450 may be a belt apparatus 451 as shown in FIG. 6C. The position control apparatus 450 may be located adjacent the drum 364 and may take the shape of at least a portion of the drum outer circumferential surface 376. The position control apparatus may hold the absorbent articles 400 in the range of 0 millimeters to about 10 millimeters from the outer circumferential surface of the drum, or between about 0.5 millimeters to about 5 millimeters from the drum outer circumferential surface.

Once the overlap area is at least partially melted, and as the drum 364 continues to rotate, the seaming station shifts to a second configuration. With reference to FIGS. 6A, 6A1, 6B, and 6B1, as previously discussed, first and second sets of cam rollers 388, 390 roll on the stationary cam track 392 as the drum 364 rotates. The stationary cam track 392 remains stationary while the first and second set of cam rollers 388, 390 roll along the stationary cam track 392. As the first and second sets of cam rollers 388, 390 roll from regions where the radius R of the stationary cam track 392 is defined by relatively shorter radii R to regions where the radius R of the stationary cam track 392 is defined by relatively longer radii R, the first, second, and third shifting links 354, 356, 385 pivot. With reference to FIG. 6B, the first shifting link 354 pivots at the base link 352 and at the cam follower member 358, while the set of second shifting links 356 pivot at the cam follower member 358 and at the base member 340. At the same time, the cam follower member 358 shifts radially outward toward the drum outer circumferential surface 376. The third shifting links 385 also pivot at the cam follower member 358, causing the heating apparatuses 384 to move radially inward, away from the drum outer circumferential surface 376, and causing the fluid nozzles 378 to spread circumferentially apart from each other on either side of the press member 380. The seaming station 348 continues to shift until the first and second set of cam rollers 388, 390 roll along regions of the stationary cam track 392 where the radius R of the stationary cam track 392 remains constant, which corresponds to the second configuration of the seaming station 348. The seaming station 348 remains in the second configuration until the first and second set of cam rollers 388, 390 travel along the stationary cam track 392 to regions where the stationary cam track is defined by relatively shorter radii.

Figure 10:
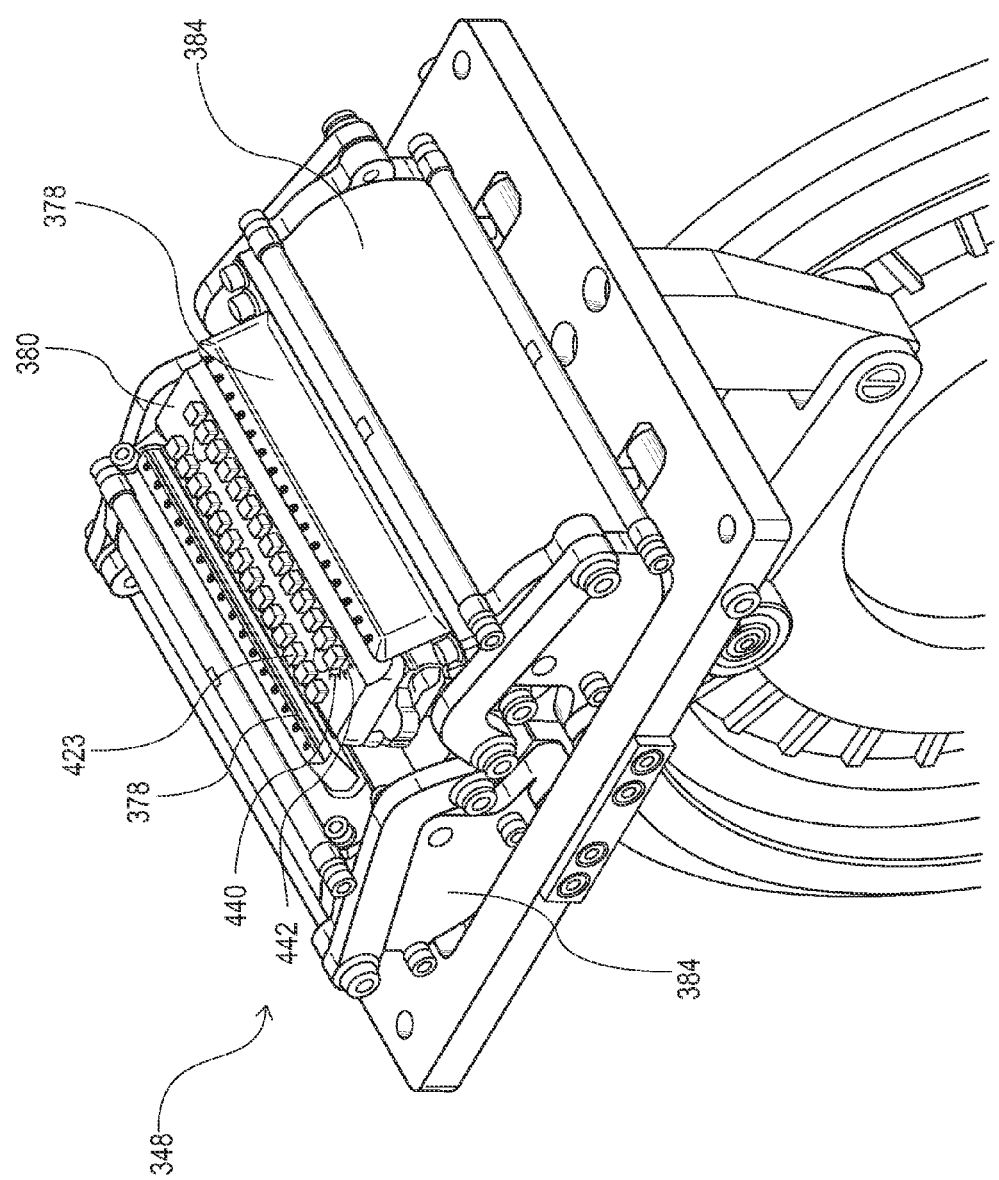
FIG. 10 is a perspective view of an embodiment of a seaming station in the second configuration.

FIG. 10 shows a perspective view of an embodiment of a seaming station 348 in the second configuration. With reference to FIG. 10, at the second configuration, the press member 380 is extending through the drum aperture beyond the drum outer circumferential surface, the heating apparatuses 384 are positioned radially inward, away from the drum aperture 366, and the fluid nozzles 378 are located on either side of the cam follower member adjacent to the drum outer circumferential surface 366.

With reference to FIGS. 6A and 6B, while the drum 364 continues to rotate and the seaming station 348 is in the second configuration, the partially melted overlap area approaches the anvil roll 368 located adjacent the drum 364. As the absorbent articles 400 pass between the anvil roll 368 and drum 364, the press member 380, which is extending through the drum aperture 366, compresses the partially melted overlap area against the anvil roll outer circumferential surface 370.

The projections 423 of the press member 380 are configured to contact the same locations of the overlap area that were at least partially melted by the heated fluid as shown in FIG. 6B, thus forming discrete bond sites 336a in the overlap area. The spring member 394 may be used to apply a predetermined force to the overlap area between the press member 380 and the anvil roll 368. Once compressed, the absorbent articles advance off of the drum outer circumferential. The drum continues to rotate and the seaming station shifts back to the first configuration in order to form discrete bond sites in a subsequent absorbent article.

In some embodiments, the bonding apparatus may compress the overlap area with multiple iterations to form discrete bond sites. For example, as shown in FIG. 6D, subsequent to compressing the overlap area the first time, the seaming station 348 shifts from the first configuration back to the second configuration as the absorbent articles 400 advance adjacent a second anvil roll 371, thereby compressing the overlap area for a second time. It is to be appreciated that multiple anvil rolls may be used and that the seaming station 348 may shift back and forth from the first configuration to the second configuration to compress the overlap area multiple times.

Figure 11:
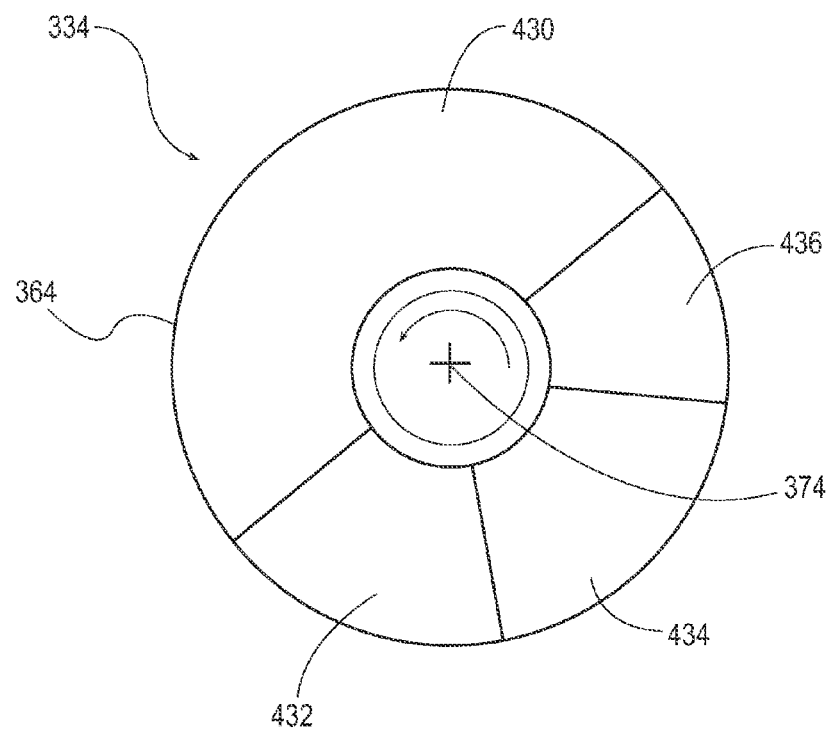
FIG. 11 is a schematic view of a bonder apparatus demonstrating the various configurations of a seaming station around a drum.

FIG. 11 shows a schematic view of the bonder apparatus 334 highlighting the various configurations of a seaming station 348 around a drum 364. As shown in FIG. 11, an individual seaming station is in a first configuration 430 for approximately 180 degrees rotation around the drum 364. Next, each seaming station transitions through a shifting configuration 432, where the seaming station shifts from a first configuration to a second configuration for approximately sixty degrees rotation around the drum 364. Each seaming station is then in a second configuration 434 for approximately sixty degrees rotation around the drum 364. And lastly, each seaming station transitions through a resetting configuration 436, where the seaming station shifts from a second configuration to a first configuration for approximately sixty degrees rotation around the drum 364. It is to be appreciated that the seaming station may be in each configuration for greater or less degrees of rotation around the drum 364 than is shown in FIG. 11.

Figure 12:
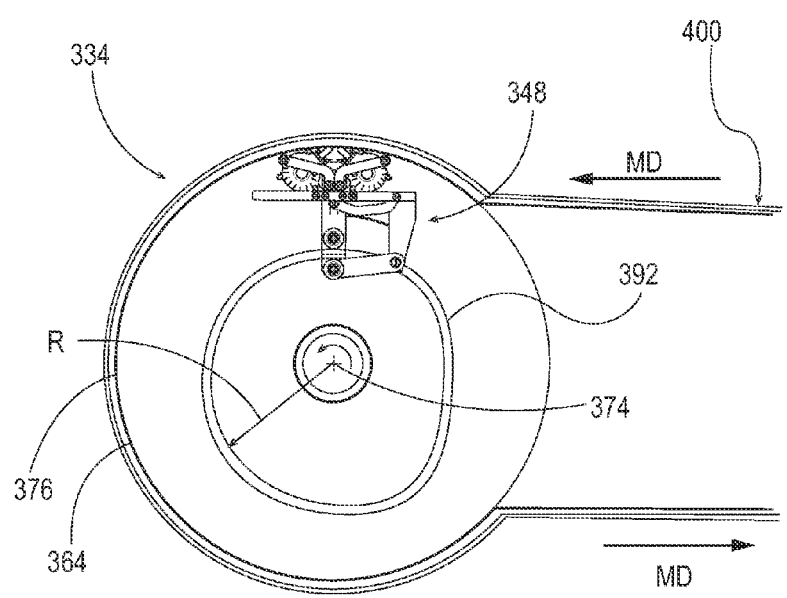
FIG. 12 is a schematic side view of a seaming station in a first configuration.
Figure 13:
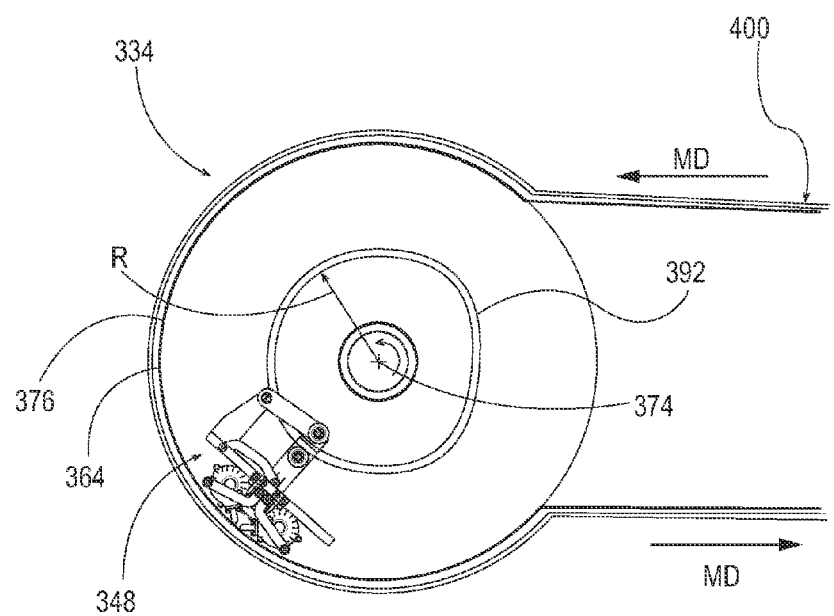
FIG. 13 is a schematic side view of a seaming station shifting from a first configuration to a second configuration.

FIG. 12 shows schematic side view of a bonder apparatus 334 with a seaming station 348 in a first configuration. As shown in FIG. 12, the seaming station 348 is in a first configuration as the absorbent articles 400 are received on the drum 364. As shown in FIG. 13, the seaming station 348 transitions from a first configuration to a second configuration at approximately 180 degrees from where the absorbent articles 400 are received on the drum 364.

Figure 14:
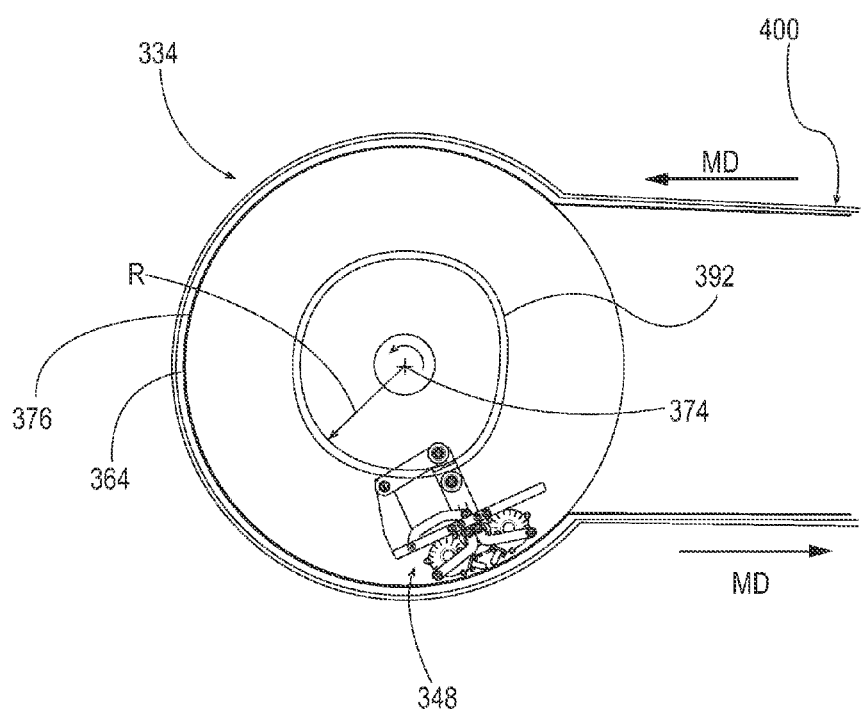
FIG. 14 is a schematic side view of a seaming station in a second configuration.
Figure 15:
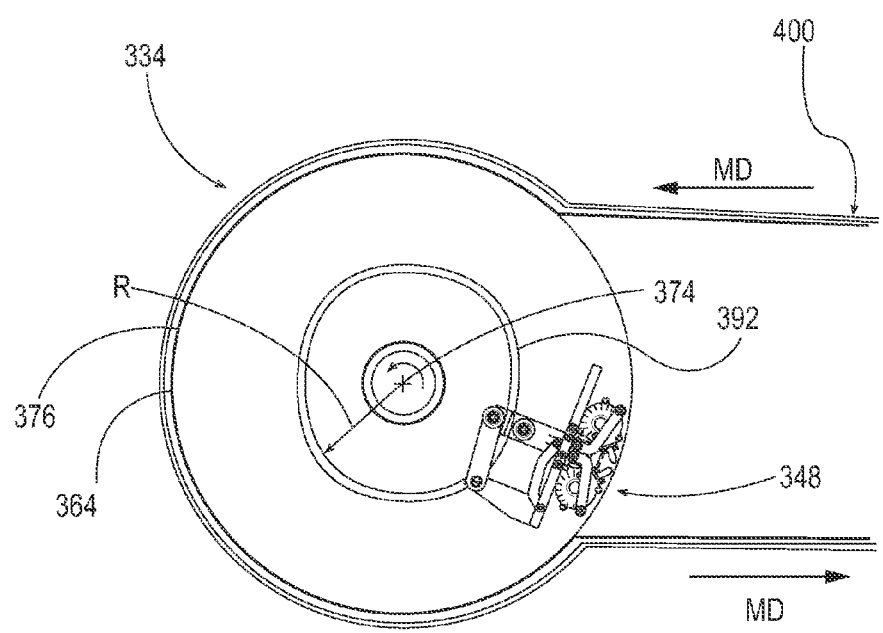
FIG. 15 is a schematic side view of a seaming station resetting from a second configuration to a first configuration.

FIG. 14 shows a schematic side view of a bonder apparatus 334 with a seaming station 348 in a second configuration. As shown in FIG. 14, the seaming station 348 is in a second configuration for approximately a sixty degree rotation around the drum 364. As shown in FIG. 15, the seaming station 348 resets from a second configuration to a first configuration after the absorbent articles 400 are advanced off of the drum 364 and before subsequent absorbent articles 400 are received on the drum 364.

Figure 16:
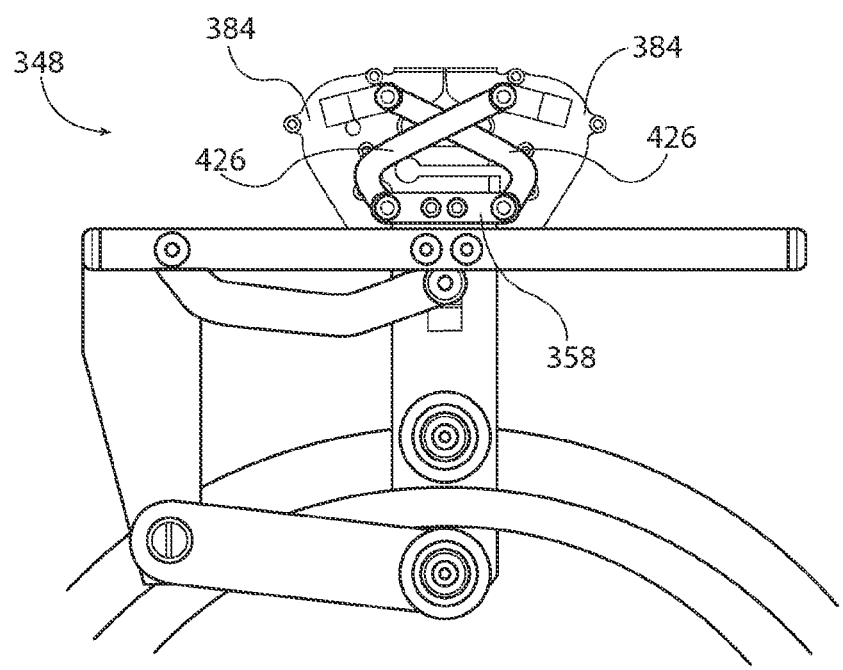
FIG. 16 is an elevation view of an embodiment of seaming station.

It is to be appreciated that the seaming station may be configured in various ways. For example, FIG. 16 shows an elevation view of an embodiment of a seaming station 348 wherein third shifting links 426 are operatively connected to a cam follower member 358 and to a heating apparatus 384. The third shifting links 426 are operatively connected to the cam follower member 358 such that at each end of the heating apparatus 384, the third shifting links 426 appear to cross paths.

In some embodiments, the distance from the absorbent articles to the fluid nozzles may range from 0 millimeters to about 20 millimeters, or between about 0 millimeters and about 5 millimeters for example, or between about 0.5 millimeters and about 3 millimeters. Control of the distance between the first and second substrate and the fluid orifice 424 may also result in a relatively more predictable fluid spray and melt pattern during the heating process.

The heated fluid may include ambient air or other gases. It is to be appreciated that the fluid may be heated to various temperatures and pressurized to various pressures. For example, in some embodiments, the fluid may be heated up to a temperature ranging from the lower melting point of first and second belt substrates minus 30° C. to the lower melting point of the first and second belt substrates plus 100° C. In some embodiments, the fluid pressure may range from $0.1 \times 10^5$ Newtons per square meter to $1 \times 10^6$ Newtons per square meter. In some embodiments, the heated fluid may be directed toward at least one of the first and second belt substrates for a time interval ranging from 10 to 1000 milliseconds or greater. Shorter or greater time intervals may be used.

In some embodiments, the press member may compress the partially melted overlap area against the anvil roll outer circumferential surface at a pressure in the range of about $1 \times 10^5$ Newtons per square meter to about $1 \times 10^8$ Newtons per square meter. In some embodiments, the press member 366 may compress the first and second belt substrates for a time period ranging from 10 to 1000 milliseconds or greater. Shorter or greater time intervals may be used.

While it is shown in FIG. 9 that each heating apparatus and fluid nozzle is one continuous element, it is to be appreciated that multiple heating apparatuses and fluid nozzles may be used. For example, each heating apparatus shown in FIG. 9 may include two or more individual heating apparatuses, each heating apparatus having a fluid nozzle. For example, an individual heating apparatus and corresponding fluid nozzle may be designed to provide heated fluid at different temperatures and pressures to different locations on the overlap area. For example, portions of the first and second belt substrates may have different number of materials and layers than other portions of the first and second belt substrate and different materials may have different melting point temperatures. By selectively heating portions with more or less pressure or at higher or lower temperatures, portions of the substrates with fewer layers or lower melting point materials will not be over-heated and portions of the substrates with more layers or higher melting point materials will not be under-heated.

As shown in FIG. 9, each fluid nozzle 378 may have a row of substantially circular fluid orifices 424. Although, it is to be appreciated that the fluid orifices 424 may be arranged in various configurations. Also, it is to be appreciated that the fluid orifice may have an oval, square, or various other shapes. The fluid orifice 424 may have a diameter ranging from about 0.1 millimeters to about 6 millimeters.

As shown in FIG. 10, the press member 380 may include substantially square-shaped projections 423 extending from the press member top face 420 in two rows. However, it is to be appreciated that the projections 423 may be regularly or irregularly spaced in various configurations and may be oriented in various directions. The projections 423 may have a circular, oval, or various other shapes. With reference to FIG. 10, the projections 423 may have a height 440 in the range of about 0.5 millimeters to about 5 millimeters. In some embodiments, the projections may have a width 442 in the range of about 2 millimeters to about 10 millimeters, or between about 4 millimeters to about 6 millimeters.

While it is shown in FIGS. 8 and 10 that the spring member 390 has a U-shape, it is to be appreciated that various other spring members may be used to absorb pressure from the press member 386 compressing the overlap area between the anvil roll outer circumferential surface. By controlling the amount of force applied to the overlap area, it is possible to apply a force sufficient to form discrete bond sites to minimize damage to the substrates and/or forming relatively weak discrete bonds.

In some embodiments, the press member and the anvil roll may be coated to prevent the at least partially melted overlap area from sticking to the surfaces of the press member and anvil roll. The press member and anvil roll may be coated with, for example, a plasma coating, polytetrafluoroethylene, or silicone. In some embodiments, the projections of the press member may have a smooth surface such that the discrete bond sites will be flat. However, in some embodiments, the projections of the press member may have a rough surface such that the discrete bond sites will have a texture.

While it is shown in FIG. 11 that the press member 386 is continuous along a press member length 387, it is to be appreciated that the press member 386 may be discontinuous along the width of the press member 386 such that multiple segments of the press member 386 may define the press member length 387. In some embodiments, multiple segments of the press member may act independently to compress the overlap area with different amounts of pressure. For example, each segment of the press member 386 may have an individual spring member 394, with each spring member 394 designed to apply a different amount of force to different parts of the overlap area. By applying different amounts of force in different locations, it may be possible to bond through different numbers of substrate layers or materials along the overlap area. By selectively compressing portions with more or less force, portions of the substrates with fewer layers or different materials will not be over compressed and portions of the substrates with more layers or different materials will not be under compressed. In some embodiments, the press member may have different shaped projections along the press member length 387, or may have more than one segment with each segment having different shaped projections, or may have different configurations of projections along the press member length.

The temperature and pressure of the fluid are maintained within a specified range once the nominal set points are selected. For example, a set point may be selected from the ranges discussed above, and the temperature may then be maintained in a fixed range around the nominal set point, such as ±30° C., and the pressure may be maintained in a fixed range around the nominal set point, such as ±1 bar. The acceptable range will depend on the relationship between the properties, such as softening point and/or melting temperature, of the materials to be joined and the nominal set point selected. For example, a nominal set point above the melting temperature of one or more of the materials to be joined may require a tighter control range than a nominal set point well below the melting temperature of one or more material to be joined. The control range may be asymmetrical about the nominal set point. By sufficiently heating, it is meant that the fluid is heated to a temperature that will enable at least partial melting, or at least softening, of the substrate or substrates. Sufficient heating may vary with the materials and equipment used. For example, if the heated fluid is applied to the substrate or substrates almost immediately, with little or no time to cool, the fluid may be heated to approximately the softening point or approximately the melting point of the substrate or substrates. If the heated fluid is directed to the substrate or substrates over some gap in time or distance, such that the heated fluid may cool somewhat before interacting with the substrate or substrates, it may be necessary to heat the fluid above, possibly significantly above, the softening point or melting point of the substrate or substrates.

The fluid may also be delivered to the overlap area with a pulsed application. The impact of the jet of heated fluid may be adjusted such that both the energy introduced by the jet plus the energy introduced by other means such as the heated anvil roll (if the anvil roll is heated), fluid nozzle, deformation of the overlap area, and the internal friction of first and second belt substrates are sufficient to at least partially melt the meltable components in first and second belt substrates to create a certain tackiness, which will form a strong joint upon compression. The melting of the meltable components may occur in a non-uniform manner throughout first and second belt substrates.

The duration of energy transfer in the process described herein may be a dynamic process, and may create a temperature gradient across the meltable components' cross sections. That is, the core of the meltable components may remain solid while the exterior surface of the meltable components melt or come close to melting. Even below the melting temperature, the exterior surface may reach a softening point, such that plastic deformation of the material may occur at a much lower load than for the same material at ambient temperature. Thus, if one or more of the materials to be joined have a softening point, the process may be adjusted to achieve a temperature in at least a portion of first and second belt substrates 406, 408 between the softening point and the melting point. The use of a temperature at or above the softening point but below the melting point of one or more of the meltable components may allow for the creation of a strong bond between first and second belt substrates 406, 408 with reduced disruption to the structure of the meltable components e.g., attenuating or otherwise weakening the meltable components.

The bonder apparatus doses and disperses thermal energy in and around the portions of the first and second belt substrates where discrete bond sites will be formed. The lower the thermal energy delivered to form the discrete bond sites, the less likely the process is to damage nearby materials, or to impact layers adjacent the intended discrete bond sites. A jet of heated fluid may be dispersed through porous layers, or, where the melting temperature of first and second belt substrates is not the same, hot air may be used to form a hole through the first outer surface, allowing penetration of the hot air to the second outer surface. Where first and second belt substrates are each porous and the first and second belt substrates have substantially the same melting temperature, a relatively low temperature, low pressure fluid stream may be used, resulting in little damage to the fibers in and around the discrete bond sites. In some instances, if one of the first and second belt substrates or another layer of material intervening between the hot fluid source and first and second belt substrates is not porous or has a melting temperature which is not substantially the same as the other layers, a relatively high temperature, high pressure fluid stream may be needed.

As discussed above, the method may further comprise the step of compressing the overlap area with a press member while the meltable components are at least partially melted, and/or in the tacky state. The temperature of the press member may be at least below the melting point of the first and second belt substrates. In some embodiments, the press member may be heated. The tackiness property of the meltable components permits the joining of the first and second belt substrates and thus, the accumulation of melted web material may be reduced or avoided. The press member may be designed according to aesthetic criteria, for example, to provide discrete, shaped points where first and second belt substrates are joined. Discrete bond sites may be configured such that the seam is relatively easier to open, if desired. The compression points may generally take the shape and spacing of the projections of the press member. As one example, the projections of the press member may be generally oval, or may have any other geometric or decorative shape consistent with the desired removal force and removal force perception. The projections of the press member may be regularly or irregularly spaced, and may be oriented in various directions.

With reference to FIGS. 4 and 5*f*, once the discrete bond sites 336*a* are formed, the absorbent articles 400 advance in the machine direction MD to a knife roll 338 where the regions 336 are cut into along the cross direction to create a first side seam 178 on an absorbent article 100 and a second side seam 180 on a subsequently advancing absorbent article. In some embodiments, it is to be appreciated that the knife roll may be integral with the press member such that as the press member compresses the overlap area, the press member also cuts the overlap area.

Although the bonding apparatus is described in the context of bonding belts to make side seams, it is to be appreciated that the methods and apparatuses herein can be used to bond various components and substrates together. The bonding apparatuses and methods herein can also be configured to operate in accordance with the apparatus and methods disclosed in U.S. Pat. No. 6,248,195 and U.S. Patent Application Publication No. 2012-0021186, filed Jun. 7, 2010.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a bond, the method comprising the steps of:
   rotating a drum about an axis of rotation, the drum comprising a fluid nozzle and a press member;
   rotating an anvil roll adjacent the drum;
   advancing a first substrate in a machine direction onto the drum, the first substrate having an inner surface and an outer surface, wherein the outer surface of the first substrate is adjacent the drum;
   advancing a second substrate in the machine direction, wherein the first substrate is between the second substrate and the drum;
   wrapping the first and second substrates around a portion of the drum;
   heating a fluid to a temperature sufficient to at least partially melt substrates;
   moving the fluid nozzle radially outward from the drum;
   directing a jet of the heated fluid onto the first and second substrates;
   partially melting the first and second substrates;
   retracting the fluid nozzle radially inward into the drum;
   shifting the press member radially outward from the drum; and
   compressing the first and second substrates between the press member and the anvil roll.

2. The method of claim 1, wherein the drum comprises a drum outer circumferential surface and a drum aperture in the drum outer circumferential surface, and wherein the fluid nozzle and press member are located radially inward from the drum aperture in the drum outer circumferential surface.

3. The method of claim 2, further comprising the step of maintaining the first and second substrates within a distance from the drum outer circumferential surface using a position control apparatus.

4. The method of claim 1, further comprising the step of maintaining the first and second substrates within a distance from the drum using a position control apparatus.

5. The method of claim 1, further comprising the step of maintaining the fluid nozzle at a distance from the first substrate.

6. The method of claim 5, wherein the distance from the fluid nozzle to the first substrate is in the range of about 0 to about 10 millimeters.

7. The method of claim 1, wherein the jet of heated fluid is at a temperature ranging from a lower melting point of the first and second substrates minus 30° C. to the lower melting point of the first and second substrates plus 100° C.

8. The method of claim 1, wherein the jet of heated fluid is directed at the first and second substrates at a pressure in the range of about $0.1 \times 10^5$ Newtons per square meter to about $1 \times 10^6$ Newtons per square meter.

9. The method of claim 1, wherein the jet of heated fluid is directed at the first and second substrates between about 10 milliseconds and about 1000 milliseconds.

10. The method of claim 1, wherein the press member compresses the first and second substrates between the anvil roll at a pressure of about $1 \times 10^5$ Newtons per square meter to about $1 \times 10^8$ Newtons per square meter.

* * * * *